United States Patent [19]

Sircar et al.

[11] 4,353,905
[45] Oct. 12, 1982

[54] SUBSTITUTED 4,5-DIHYDRO-6-[4-(1H-IMIDAZOL-1-YL)PHENYL]-3(2H)-PYRIDAZINONES AND 6-[4-(1H-IMIDAZOL-1-YL)PHENYL]-3(2H)-PYRIDAZINONES

[75] Inventors: Ila Sircar; James A. Bristol, both of Ann Arbor, Mich.

[73] Assignee: Warner-Lambert Company, Morris Plains, N.J.

[21] Appl. No.: 302,181

[22] Filed: Sep. 17, 1981

[51] Int. Cl.³ .................. C07D 403/10; A61K 31/50
[52] U.S. Cl. .................................. 424/250; 544/239; 548/336; 548/341; 548/346; 424/273 R
[58] Field of Search .................. 548/336, 341, 346; 544/239, 238; 424/250

[56] References Cited

U.S. PATENT DOCUMENTS

| 3,845,050 | 10/1974 | Lebkuecher et al. | 544/239 |
| 4,088,762 | 5/1978 | Hakim et al. | 424/250 |
| 4,251,658 | 2/1981 | Szilagyi et al. | 544/238 |
| 4,301,169 | 11/1981 | Yamanaka et al. | 424/273 |

FOREIGN PATENT DOCUMENTS

| 8391 | 8/1978 | European Pat. Off. | |
| 12366 | 12/1978 | European Pat. Off. | |
| 2151216 | 4/1973 | Fed. Rep. of Germany | |
| 51-1043776 | 4/1976 | Japan | 544/239 |
| 54-4019987 | 2/1979 | Japan | 544/239 |
| 2057438 | 8/1980 | United Kingdom | |

*Primary Examiner*—Donald G. Daus
*Assistant Examiner*—G. Hendricks
*Attorney, Agent, or Firm*—Walter Patton

[57] ABSTRACT

Substituted 4,5-dihydro-6-[4-(1H-imidazol-1-yl)-phenyl]-3(2H)-pyridazinone compounds and 6-[4-(1H-imidazol-1-yl)phenyl]-3(2H)-pyridazinone compounds and pharmaceutically acceptable salts thereof are useful as cardiotonic agents.

Said compounds cause a significant increase in myocardial contractility in the anesthetized dog. Said compounds are produced by reacting substituted γ-oxo-benzenebutanoic acids with suitably substituted hydrazines to provide 4,5-dihydro-6-[4-(1H-imidazol-1-yl)phenyl]-3(2H)-pyridazinones which are dehydrogenated to 6-[4-(1H-imidazol-1-yl)phenyl]-3(2H)-pyridazinones.

Both the intermediate 4,5-dihydro-6-[4-(1H-imidazol-1-yl)phenyl]-3(2H)-pyridazinones and the 6-[4-(1H-imidazol-1-yl)phenyl]-3(2H)-pyridazinones are useful as cardiotonic agents.

6 Claims, No Drawings

SUBSTITUTED 4,5-DIHYDRO-6-[4-(1H-IMIDAZOL-1-YL)PHENYL]-3(2H)-PYRIDAZINONES AND 6-[4-(1H-IMIDAZOL-1-YL)PHENYL]-3(2H)-PYRIDAZINONES

BACKGROUND OF THE INVENTION

The present invention relates to 4,5-dihydro-6-[4-(1H-imidazol-1-yl)phenyl]-3(2H)-pyridazinone compounds and 6-[4-(1H-imidazol-1-yl)phenyl]-3(2H)-pyridazinone compounds useful as cardiotonic agents.

SUMMARY OF THE INVENTION

The present invention relates to novel substituted 4,5-dihydro-6-[4-(1H-imidazol-1-yl)phenyl]-3(2H)-pyridazinone compounds and 6-[4-(1H-imidazol-1-yl)phenyl]-3(2H)-pyridazinone compounds useful as cardiotonic agents having the structural formula (I):

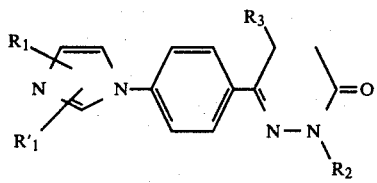

wherein $===$ represents a double or single bond between two carbon atoms; $R_1$ and $R_1'$ are independently hydrogen, lower alkyl, $CH_2C_6H_5$ or $C_6H_5$; $R_2$ is hydrogen, lower alkyl or 2-hydroxyethyl; $R_3$ is hydrogen, lower alkyl wherein lower alkyl contains one to six carbon atoms; and the pharmaceutically acceptable salts thereof.

The compounds of formula I where $R_2$ is hydrogen may exist in tautomeric forms, that is, as 6-[4-(1H-imidazol-1-yl)phenyl]-3(2H)-pyridazinones of formula I and/or as 6-[4-(1H-imidazol-1-yl)phenyl]-3-pyridazinols of formula IA, illustrated as follows.

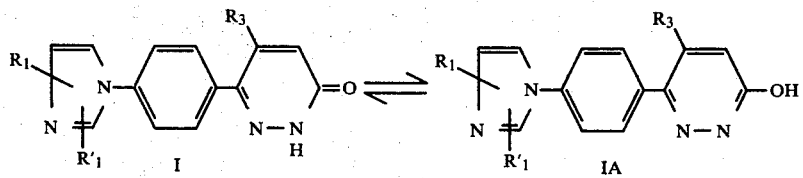

The present invention also relates to 4,5-dihydro-6-[4-(1H-imidazol-1-yl)phenyl]-3(2H)-pyridazinones having the structural formula (II):

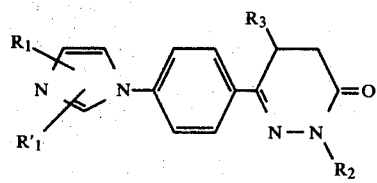

wherein $R_1$, $R_1'$, $R_2$, and $R_3$ are as defined above.

These compounds are not only useful as intermediates for preparing the compounds of formula I but are also useful as cardiotonic agents.

The present invention further relates to the method for increasing cardiac contractility in a patient requiring such treatment which comprises administering orally or parenterally in a solid or liquid dosage form to such patient an effective amount of compounds having the structure (I).

Another aspect of the present invention relates to a cardiotonic composition for increasing cardiac contractility, said composition comprising an effective amount of the compound of formula (I) and a pharmaceutically acceptable carrier.

The present invention further relates to a method for increasing cardiac contractility which comprises the administration of a medicament comprising an effective amount of the compound of formula (I) and a pharmaceutically acceptable carrier.

The process for producing 6-[4-(1H-imidazol-1-yl)phenyl]-3(2H)-pyridazinones comprises reacting substituted 4-(1H-imidazol-1-yl)-γ-oxo benzenebutanoic acids with suitably substituted hydrazines to give 4,5-dihydro-6-[4-(1H-imidazol-1-yl)phenyl]-3(2H)-pyridazinones which can be dehydrogenated to the desired product by known dehydrogenation procedures such as bromination-dehydrobromation; by noble metal catalyzed dehydrogenation such as palladium-catalyzed dehydrogenation or by oxidation-reduction procedures using m-nitrobenzenesulphonic acid as the reagent according to the standard literature procedure set forth by W. V. Curran and Adma Ross, *J. Med. Chem.*, 17, 273 (1974).

The compounds of formula (I) are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate or methanesulfonate salts. However, other appropriate pharmceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate and the like respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The following Examples will further illustrate the invention without, however, limiting it thereto.

EXAMPLE 1

Methyl 4-(1H-imidazol-1-yl)-β-oxobenzenepropanoate

A solution of 4-(1H-imidazol-1-yl)acetophenone (24.2 g, 0.13 mol) in tetrahydrofuran (250 ml) is added to a suspension of 50% NaH (6.7 g) in tetrahydrofuran (70 ml) with stirring. The solution is stirred at room temperature for one hour. Dimethylcarbonate (30 ml) is added followed by refluxing the mixture overnight. The solid is filtered off, the residue is treated with water, and neutralized with acetic acid. The solid thus obtained is filtered off and crystallized from a methanol-ether mixture to yield 15.0 g of the product methyl-4-(1H-imidazol-1-yl)-β-oxobenzenepropanoate.

EXAMPLE 2

4-(1H-imidazol-1-yl)-γ-oxobenzenebutanoic acid

A solution of methyl 4-(1H-imidazol-1-yl)-β-oxobenzenepropanoate (6.1 g, 0.025 mol) in tetrahydrofuran (65 ml) is added slowly to a stirred suspension of 50% NaH (1.2 g, 0.025 mol) in tetrahydrofuran (20 ml) and the solution is stirred for one additional hour. Ethyl bromoacetate (4.5 g) is added followed by refluxing the mixture for 7 to 8 hours. The tetrahydrofuran is removed, the residue is treated with water, and the organic material is extracted with ether. The residue obtained after removal of ether is hydrolysed by heating with 6 N HCl for 7 to 8 hours. The crude acid is finally crystallized from dimethylformamide to yield 3.3 g of the product 4-(1H-imidazol-1-yl)-γ-oxobenzenebutanoic acid.

EXAMPLE 3

4,5-dihydro-6-[4-(1H-imidazol-1-yl)phenyl]-3(2H)-pyridazinone

A solution of 4.5 g of 4-(1H-imidazol-1-yl)-γ-oxobenzenebutanoic acid in ethanol (60 ml) is heated under reflux with 85% hydrazine hydrate (2.5 ml) for 17 hours. The alcohol is evaporated off, the residue is treated with water and filtered. The crude product is finally crystallized from ethanol to yield 3.5 g of the product 4,5-dihydro-6-[4-(1H-imidazol-1-yl)phenyl]-3(2H)-pyridazinone: mp. 206°-207° C.(dec.)

Anal. calcd for $C_{13}H_{12}N_4O$; C, 65.00; H, 5.00; N, 23.33. Found; C, 65.06; H, 5.35; N, 23.39.

Similarly, reaction of 4-(2-methyl-1H-imidazol-1-yl)-γ-oxobenzenebutanoic acid with hydrazine hydrate according to the procedure of this Example gives 4,5-dihydro-6-[4-(2-methyl-1H-imidazol-1-yl)phenyl]-3(2H)-pyridazinone.

Similarly, reaction of 4-(2-phenyl-1H-imidazol-1-yl)-γ-oxobenzenebutanoic acid with hydrazine hydrate according to the procedure of this Example gives 4,5-dihydro-6-[4-(2-phenyl-1H-imidazol-1-yl)phenyl]-3(2H)-pyridazinone.

Similarly, reaction of 4-(2-ethyl-4-methyl-1H-imidazol-1-yl)-γ-oxobenzenebutanoic acid with hydrazine hydrate according to the procedure of this Example gives 4,5-dihydro-6-[4-(2-ethyl-4-methyl-1H-imidazol-1-yl)-phenyl]-3(2H)-pyridazinone.

Using the procedure of this Example, reaction of 4-(1H-imidazol-1-yl)-γ-oxobenzenebutanoic acid with methyl hydrazine and 2-hydroxyethyl hydrazine gives 4,5-dihydro-2-methyl-6-[4-(1H-imidazol-1-yl)phenyl]-3(2H)-pyridazinone and 4,5-dihydro-2-(2-hydroxyethyl)-6-[4-(1H-imidazol-1-yl)phenyl]-3(2H)-pyridazinone respectively.

EXAMPLE 4

6-[4-(1H-imidazol-1-yl)phenyl]-3(2H)-pyridazinone

Bromine (1.6 ml) is added dropwise to a solution of 4,5-dihydro-6-[4-(1H-imidazol-1-yl)phenyl]-3(2H)-pyridazinone (3.5 g) in acetic acid (25 ml) at 80° C. The mixture is heated for 5 to 6 hours to complete the reaction. The solid is filtered, washed with ether and converted to the free base which is crystallized from ethanol to yield 1.1 g of the product 6-[4-(1H-imidazol-1-yl)phenyl]-3(2H)-pyridazinone: mp. 244°-245° C.

Anal. calcd for $C_{13}H_{10}N_4O.1/5H_2O$; C, 64.56; H, 4.30; N, 23.17; $H_2O$, 1.49. Found; C, 64.30; H, 4.36; N, 23.04; $H_2O$, 1.11.

Similarly, reaction of 4,5-dihydro-6-[4-(2-methyl-1H-imidazol-1-yl)phenyl]-3(2H)-pyridazinone with bromine in acetic acid as described in this Example gives 6-[4-(2-methyl-1H-imidazol-1-yl)phenyl]-3(2H)-pyridazinone.

Similarly, reaction of 4,5-dihydro-6-[4-(2-phenyl-1H-imidazol-1-yl)phenyl]-3(2H)-pyridazinone with bromine in acetic acid as described in this Example gives 6-[4-(2-phenyl-1H-imidazol-1-yl)phenyl]-3(2H)-pyridazinone.

Similarly, reaction of 4,5-dihydro-6-[4-(2-ethyl-4-methyl-1H-imidazol-1-yl)phenyl]-3(2H)-pyridazinone with bromine in acetic acid as described in this Example gives 6-[4-(2-ethyl-4-methyl-1H-imidazol-1-yl)phenyl]-3(2H)-pyridazinone.

Using the procedure of this Example, reaction of 4,5-dihydro-2-methyl-6-[4-(1H-imidazol-1-yl)phenyl]-3(2H)-pyridazinone and 4,5-dihydro-2-[2-hydroxyethyl]-6-[4-(1H-imidazol-1-yl)phenyl]-3(2H)-pyridazinone with bromine in acetic acid gives 2-methyl-6-[4-(1H-imidazol-1-yl)phenyl]-3(2H)-pyridazinone and 2-[2-hydroxyethyl]-6-[4-(1H-imidazol-1-yl)phenyl]-3(2H)-pyridazinone respectively.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test for in vivo Myocardial Inotropic Activity in Anesthetized Dog

This screen consists of determining the effects of increasing intravenous doses of compound on myocardial contractility (dP/dt max of left ventricular blood pressure), heart rate and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min cause dose related significant increases in cardiac contractility with only low or minimal changes in heart rate and blood pressure.

Test Results of
4,5-dihydro-6-[4-(1$\underline{H}$-imidazol-1-yl)phenyl]-3(2$\underline{H}$)-pyridazinone Using Anesthetized Dog Procedure

| Dose mg/kg | % Change Myocardial Contractility | Heart Rate | Blood Pressure |
|---|---|---|---|
| 0.01 | 9 | −4.0 | −2.0 |
| 0.03 | 32 | −4.0 | −6.0 |
| 0.10 | 57 | −1.0 | −10.5 |
| 0.31 | 87 | 2.0 | −21.5 |

Test Results of
6-[4-(1$\underline{H}$-imidazol-1-yl)phenyl]-3(2$\underline{H}$)-pyridazinone Using Anesthetized Dog Procedure

| Dose mg/kg | % Change Myocardial Contractility | Heart Rate | Blood Pressure |
|---|---|---|---|
| 0.01 | 3 | 0.0 | 0.0 |
| 0.03 | 15 | 6.0 | −1.5 |
| 0.10 | 40 | 16.0 | −6.0 |
| 0.31 | 78 | 32.0 | −9.0 |

The actual determination of the numerical cardiotonic data definitive for any other particular compound of the invention is readily obtained according to the above-described standard test procedure by those skilled in pharmacological test procedures, without any need for any extensive experimentation.

The present invention includes within its scope a cardiotonic composition for increasing cardiac contractility, said composition comprising a pharmaceutically acceptable carrier and, as the active component thereof, a cardiotonic compound of the present invention or pharmaceutically acceptable acid addition salt thereof. The invention also includes within its scope the method for increasing cardiac contractility in a patient requiring such treatment which comprises administering to such patient an effective amount of a compound of the present invention or pharmaceutically acceptable acid addition salt thereof. In clinical practice the said compounds of the present invention will normally be administered orally or parenterally in a wide variety of dosage forms.

Solid compositions for oral administration include compressed tablets, pills, powders, and granules. In such solid compositions, at least one of the active compounds is admixed with at least one inert diluent such as starch, calcium carbonate, sucrose or lactose. These compositions may also contain additional substances other than inert dilutents, e.g., lubricating agents such as magnesium stearate, talc and the like.

Liquid compositions for oral administration include pharmaceutically acceptable emulsions, solutions, suspensions, syrups, and elixirs containing inert diluents commonly used in the art, such as water or liquid paraffin. Besides inert diluents such compositions may also contain adjuvants, such as wetting and suspending agents, and sweetening, flavoring, perfuming, and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous organic, and organic solutions, suspensions and emulsions. Examples of organic solvents or suspending media are propylene glycol, polethylene glycol, vegetable oils such as olive oil and injectable organic esters such as ethyl oleate. These compositions may also contain adjuvants such as stabilizing, preserving, wetting, emulsifying and dispersing agents.

They may be sterilized, for example by filtration through a bacteria-retaining filter, by incorporation of sterilizing agents in the compositions, by irradiation or by heating. They may also be manufactured in the form of sterile solid compositions which can be dissolved in sterile water or some sterile injectable medium immediately before use.

The percentage of active component in the said composition and method for increasing cardiac contractility may be varied so that a suitable dosage is obtained. The dosage administered to a particular patient is variable, depending upon the clinician's judgment using as the criteria: The route of administration, the duration of treatment, the size and condition of the patient, the potency of the active compound and the patient's response thereto. An effective dosage amount of active component can thus only be determined by the clinician considering all criteria and utilizing his best judgment on the patient's behalf.

What is claimed is:

1. A compound having the structural formula:

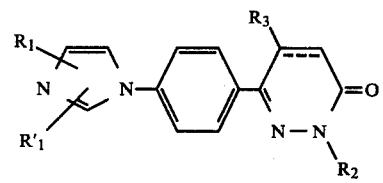

wherein $=\!=\!=$ represents a double or single bond between two carbon atoms; $R_1$ and $R_1'$ are independently hydrogen, lower alkyl, $CH_2C_6H_5$ or $C_6H_5$; $R_2$ is hydrogen, lower alkyl or 2-hydroxyethyl; and $R_3$ is hydrogen or lower alkyl wherein lower alkyl has one to six carbon atoms; and the pharmaceutically acceptable salts thereof.

2. A compound according to claim 1 having the structure:

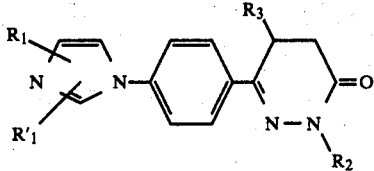

wherein $R_1$, $R_1'$, $R_2$, and $R_3$ are as defined in claim 1, and the pharmaceutically acceptable salts thereof.

3. A compound according to claim 1 having the structure:

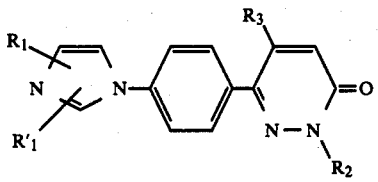

wherein $R_1$, $R_1'$, $R_2$, and $R_3$ are as defined in claim 1, and the pharmaceutically acceptable salts thereof.

4. A compound according to claim 2 which is 4,5-dihydro-6-[4-(1H-imidazol-1-yl)phenyl]-3(2H)-pyridazinone.

5. A compound according to claim 3 which is 6-[4-(1H-imidazol-1-yl)phenyl]-3(2H)-pyridazinone.

6. The method for increasing cardiotonic contractility in a patient requiring such treatment which comprises administering orally or parenterally in a solid or liquid dosage form to such patient an effective amount of a compound having the structure:

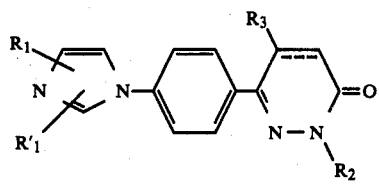

wherein $=\!=\!=$ represents a single or double bond between two carbon atoms; $R_1$, and $R_1'$ are independently hydrogen, lower alkyl, $CH_2C_6H_5$ or $C_6H_5$; $R_2$ is hydrogen, lower, alkyl, 2-hydroxyethyl; $R_3$ is hydrogen or lower alkyl; or a pharmaceutically acceptable acid addition salt thereof.

* * * * *